United States Patent [19]

Usami et al.

[11] Patent Number: 4,678,773
[45] Date of Patent: Jul. 7, 1987

[54] ANTITUMOR AGENT

[75] Inventors: Hiroko Usami; Akihiro Yamamoto, both of Tokyo; Yutaka Sugawara, Saitama; Shozo Kotani, Osaka; Keijiro Kato, Okayama, all of Japan

[73] Assignee: Chugai Seiyaku Kabushiki Kaisha, Tokyo, Japan

[21] Appl. No.: 641,217

[22] Filed: Aug. 16, 1984

[30] Foreign Application Priority Data

Aug. 26, 1983 [JP] Japan ................................ 58-155010
Aug. 26, 1983 [JP] Japan ................................ 58-155011

[51] Int. Cl.$^4$ .................... A61K 31/70; A61K 31/66; A61K 31/045; A61K 39/02
[52] U.S. Cl. .................................. 514/25; 514/103; 514/738; 424/92; 424/195.1; 536/17.1
[58] Field of Search .................... 424/92, 195; 514/25, 514/138, 103; 536/17.1

[56] References Cited

PUBLICATIONS

14th International Congress of Chemotherapy Abstract Sy-6-6, Niitsu et al., 1985.
Pennica et al., Nature 312; 724–729, 1984.
Chem. Abstr. 85:92092n, 1976.
Wicken, Anthony J. and Knox, Kenneth W., Biological Properties of Lipoteichoic Acids, Microbiology, 360–365, 1977.
Wicken, A. J. and Knox, K. W., Immunological Properties of Teichoic Acids, Bact. Rev., vol. 37: 215–257, 1973.
Wicken, A. J. and Knox, Kenneth W., Lipoteichoic Acids: A New Class of Bacterial Antigen, Science, vol. 187, pp. 1161–1167, 1975.
E. A. Carswell, L. J. Old, R. L. Kassel, S. Green, N. Fiore, and B. Williamson, An Endotoxin-Induced Serum Factor that causes Necrosis of Tumors, P.N.A.S. vol. 72:, 3666–3670, 1975.

*Primary Examiner*—Johnnie R. Brown
*Assistant Examiner*—John W. Rollins
*Attorney, Agent, or Firm*—Browdy and Neimark

[57] ABSTRACT

An antitumor agent of the present invention comprises, as an effective ingredient, lipoteichoic acid which is extracted from gram-positive bacterial cells.

11 Claims, 2 Drawing Figures

ANTITUMOR AGENT

FIELD OF THE INVENTION

This invention relates to an antitumor agent comprising lipoteichoic acids (hereafter referred to AS LTA) as an effective ingredient.

PRIOR ART

LTA is a group of amphipathic substances found in gram-positive bacterial cells. LTA consists of a polymer chain of polyglycerophosphate (PGP) as a backbone structure and glycolipids of cytoplasmic membrane origin (A. J. Wicken et al., Biological Properties of Lipoteichoic Acids, *Microbiology*, pp 360–365, 1977).

Electronmicroscopic analysis by ferritin labelled antibody technique reveals that the one end of the LTA is linked to cytoplasmic membrane glycolipid while the other end of the LTA extends to the cell outer surface of the bacteria through the cell wall peptidoglycan layer.

Examples of gram positive bacteria having LTA are those belonging to such genera as Streptococcus, Micrococcus, Lactobacillus, Staphylococcus, Bacillus and Listeria. The structures of LTA may partially differ among bacteria of different genera or even among different species of the same genus. For example, differences in length (25–30) of PGP chain, or in number or type of sugar residues in the glycolipid moiety are known.

LTA has not been fully studied with respect to its immunopharmacological activities. In particular, the use of LTA for treatment of tumor patients has never been reported.

SUMMARY OF THE INVENTION

The present inventors have found that LTA has an excellent antitumor activity without causing any side effects in animals.

The main object of the present invention is to provide an antitumor agent comprising LTA as an effective ingredient together with a suitable diluent or carrier.

Other objects of the invention will become clear by reading the following description.

DETAILED DESCRIPTION OF THE INVENTION

Figure 1:
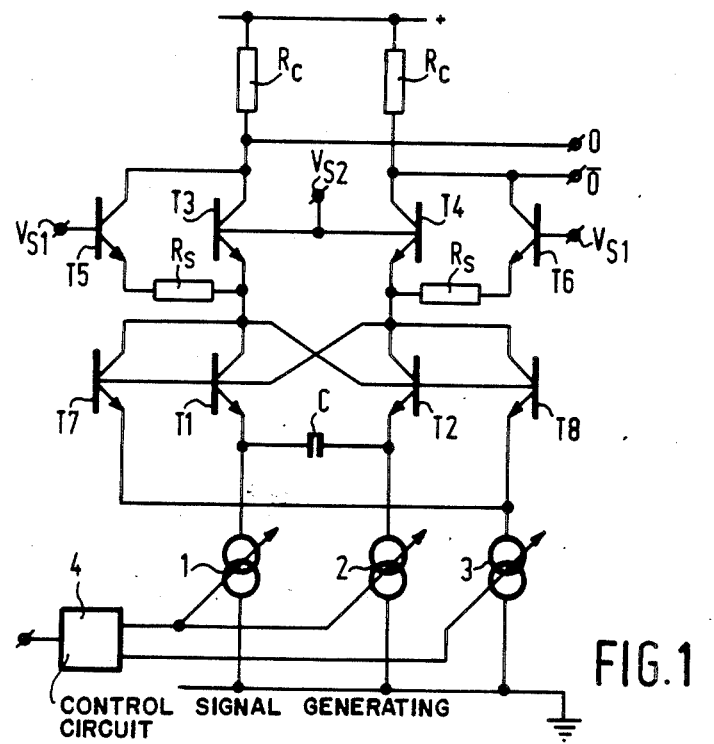
FIG. 1 shows the antitumor activity of LTA in Example 1.

Partial structural differences of LTA do not have serious influence on its biological activities. Thus LTA from any species or genera of gram-positive bacteria has good possibility to serve as an antitumor agent of the present invention.

For example, LTA obtained from *Streptococcus pyogenes*, which contains 0.5 mole alaine, 0.82 mole phosphoric acid, 0.05 mole glucose and 0.012 mole fatty acids relative to 1 mole of glycerol, may be conveniently employed.

Examples of bacterial strains having such LTA and which may be used in the present invention are as follows:

*Streptococcus faecalis*
*Streptococcus pyogenes*
*Streptococcus mutans*
*Streptococcus lactis*
Streptococcus equisimilis (FERM-P 4059)
*Streptococcus sanguis*
*Staphylococcus aureus*
*Staphylococcus epidermidis*
*Lactobacillus plantarum*
*Lactobacillus fermentum*
*Lactobacillus casei*
*Listeria monocytogenes.*

The preparation of LTA from whole cells, or a cell envelope fraction of these bacteria may be obtained, for example, according to the method described by Beachey et al. (Infect. Immun., 23, 618–625, 1979).

LTA is soluble in both water and a lipophilic medium because of its amphipathic property. Therefore, it can be formulated by a conventional formulation process into any desired form such as an oral agent or a parentheral agent containing a desired amount of the active ingredient.

Examples of carriers which may be used for formulating such agents are crystalline cellulose, corn starch, sugars such as glucose and lactose, magnesium stearate and calcium stearate.

In general, for good antitumor effects to be obtained in man, 0.1–100 mg, preferably 1–20 mg of LTA is administered to an adult as a daily dosage unit in the agent of the present invention.

PREPARATION EXAMPLE

*Streptococcus pyogenes* SV strain (ATCC 21059) was cultured in Todd Hewitt broth (Difco, USA) overnight. Cells were collected and disrupted by a Braun cell homogenizer. A fraction of cell envelopes was collected by centrifugation and it was suspended in distilled water at 10 mg (dry weight)/ml. An equal volume of 95% phenol was added to the suspension, and extraction of LTA was conducted by gentle stirring at a temperature between 4° C. and room temperature for an hour. The water phase was separated by centrifugation (18000×g) for 30 minutes. An equal volume of water was added to the remaining phenol phase to repeat the extraction twice in the same manner. All of the water phases were combined and after being fully dialysed against distilled water, the combined water phase was lyophilized to obtain a crude LTA preparation.

The crude LTA was dissolved in 0.2M ammonium acetate at a concentration of 50 mg (dry weight)/ml, which was then applied to a gel filtration column (2.6 $\phi \times 87$ cm) of Sepharose 6B (Pharmacia Co., Sweden) and was fractionated with 0.2M ammonium acetate as an eluant, whereby the crude LTA was purified. Each effluent was monitored by its activity to sensitize sheep red blood cells (SRBC) to be agglutinated by anti-PGS serum, and by a colorimetric determination of phosphorus to determine the localization of LTA.

EXAMPLE 1

Anti-tumor effect of streptococcal LTA on solid-type Meth-A fibrosarcoma

Groups of 5 female, 6 week-old BALB/c mice (purchased from Charles River Japan Inc., Japan) were transplated at the abdominal region intradermally with a suspension of Meth-A fibrosarcoma cells ($2 \times 10^5$/mouse). LTA obtained in the Preparation Example was dissolved in physiological saline and 0.2 ml of the solution was intraperitoneally administered daily for four successive days from the day after the tumor inoculation. Mice of the control group were administered with physiological saline (0.2 ml) in place of the LTA solution.

To evaluate antitumor activity, tumor size was determined in terms of $\sqrt{\text{length} \times \text{width}}$ at intervals and growth inhibition rate was obtained as a ratio of average tumor sizes in the LTA group and the control group.

The result is shown in FIG. 1. A significant antitumor effect was observed 22 days after the transplantation in the group administered with 10 µg and 2 µg of LTA.

EXAMPLE 2

Anti-tumor effect of streptococcal LTA on ascites type Meth-A fibrosarcoma

Groups of 5 mice of the same strain as used in Example 1 were transplanted in their peritoneal cavities with $2 \times 10^5$ cells of Meth-A fibrosarcoma.

LTA solution obtained in the preparation Example was administered into mice in the same method as described in Example 1.

The anti-tumor effect was expressed by the following formula:

$$\frac{\text{Mean survival days of LTA-treated mice}}{\text{Mean survival days of control mice}}$$

Figure 2:
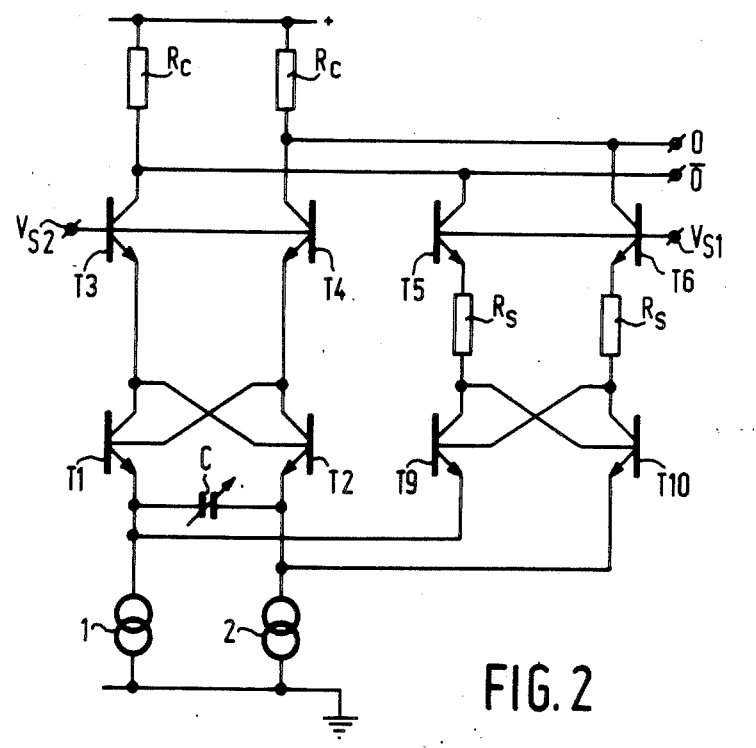
FIG. 2 shows the antitumor activity of LTA in Example 2.

As shown in FIG. 2, the anti-tumor effect of LTA was definitely observed in mice with ascites type of Meth-A fibrosarcoma. In addition, two out of five mice in each of the test groups which are given the injection of 10 µg or 50 µg of LTA were still surviving 60 days after the tumor inoculation, while all mice in the control group died within 24 days.

EXAMPLE 3

Anti-tumor effect of Lactobacillary LTA on solid-type Meth-A fibrosarcoma

Anti-tumor effect was studied as described in Example 1 using LTA which was obtained from *Lactobacillus plantarum* according to the method described in the Preparation Example. As shown in FIG. 3, LTA from *L. plantarum* also has an antitumor effect on solid-type Meth-A fibrosarcoma.

The chemical composition of the LTA is shown in Table 1.

TABLE 1

| Chemical Composition of LTA-fraction of *L. plantarum* ATCC 8014 | | |
|---|---|---|
| | LTA-fraction | |
| Component | % | Mole ratio |
| Hexose | 15.2 | 0.27 |
| Glycerol | 28.4 | 1.00 |
| Phosphorus | 34.4 | 1.15 |
| Protein | — | |
| Pentose | 0.16 | 0.003 |
| Fatty acids | 7.3 | 0.08 |
| Methylpentose | 2.9 | 0.05 |
| Alanine | Not determined | |

The foregoing Examples 1-3 clearly show the definite anti-tumor effect of LTA.

As one of the approaches to studying the mechanism of the anti-tumor effect of LTA, the present inventors have examined a possible activity of LTA to induce tumor necrotizing factor (TNF), and have found that LTA is a potent inducer of TNF as described in Example 4. TNF is a substance found in the serum of LPS treated animals which had been primed by previous injection of B.C.G. or *Propionibacterium acnes* TNF causes necrosis of some animal tumors in vivo, and is cytotoxic or cytostatic to tumor cell lines of animal and human origin in vitro. The above finding suggests that the anti-tumor effect of LTA may be at least partly due to the TNF-inducing activity of LTA.

EXAMPLE 4

Induction of TNF by LTA in mice primed with *P. acnes*

(1) Preparation of TNF

A group of 8 female, 5 week-old ICR mice (purchased from Charles River Japan Inc.) were given an intraperitoneal injection of formalin-killed cells (1.5 mg/mouse) of *P. acnes*.

On the 11th day, the mice received an intravenous injection of LTA (100 µg/mouse) obtained in the Preparation Example. Two hours later, the mice were bled and a serum was prepared by a conventional method. Serum specimens were prepared also from groups treated only with *P. acnes* or LTA as well as from a non-treated group. Each serum was centrifuged ($39,000 \times g$) for an hour. The upper one third portion of the supernatant was discarded and TNF activity of the serum was measured using the lower two thirds portion of the supernatant (hereafter referred to as LTA-induced TNF).

(2) Cytotoxic activity of LTA-induced TNF on L-cells

A suspension of L-929 cell ($1 \times 10^5$ cells/ml) in RPMI-1640 medium supplemented with 10% FCS (fetal calf serum) was distributed in a microplate having 96 wells (80 µl/well), and the cells were incubated for 3 hours at 37° C. under at atmosphere of 5% $CO_2$-air. Then 100 µl of the TNF sample obtained in above (1) which was serially 5 fold diluted with an RPMI-1640 medium containing FCS and 20 µl $^3$H-thymidine solution (1 µ$C_i$) was added to the cells in each well. The cells were then cultured at 37° C. under 5% $CO_2$-air.

The medium was discarded after 48 hours and the L-929 cells were collected with a cell harvester after being released from the plate by trypsin-EDTA method so as to enable the radioactivity (c.p.m) of $^3$H-thymidine uptaken in the cells to be counted.

The cytotoxic effect of streptococcal LTA-induced TNF on L-929 cells in terms of the activity to inhibit thymidine uptake is shown in Table 2.

TABLE 2

| Cytotoxic effect of streptococcal LTA-induced TNF on L-cells | | | |
|---|---|---|---|
| Serum specimen from mice treated with[a] | | | |
| *P. acnes* | LTA | $^3$H—Thymidine uptake[b] | % Inhibition[c] |
| — | — | 22.632 ± 363 | −3.0 |
| + | — | 20.740 ± 668 | 5.5 |
| — | + | 20.559 ± 357 | 6.4 |
| + | + | 5.766 ± 88 | 73.7 |
| RPMI-1640 | | 21.955 ± 540 | 0 |

TABLE 2-continued

Cytotoxic effect of streptococcal
LTA-induced TNF on L-cells

| Serum specimen from mice treated with[a] | | $^3$H—Thymidine uptake[b] | % Inhibition[c] |
|---|---|---|---|
| P. acnes | LTA | | | with 10% FCS

[a]Serum samples diluted 1:200 with RPMI-1640 containing 10% FCS were submitted to the assay.
[b]$^3$H—thymidine uptake was expressed as mean ± standard error (S.E.) in triplicate. Background count (235 c.p.m.) was subtracted from each determination.
[c]Percent inhibition of thymidine uptake was calculated by the equation:

$$\left(1 - \frac{\text{c.p.m. of test group}}{\text{c.p.m. of control group}}\right) \times 100\ (\%)$$

Several other mouse tumor cell lines were examined for their susceptibility to the cytotoxic effect of LTA-induced TNF in the same system as described above. The results are shown in Table 3.

TABLE 3

Cytotoxic effect of Streptococcal LTA-induced TNF on various tumor cell lines

| Cell line | Growth inhibition (%) P. acnes-LTA | |
|---|---|---|
| | 1/100[a] | 1/1000[a] |
| Meth-A | 66.5** | 43.7** |
| EL-4 | 51.4** | 9.8 |
| BAMC-1 | 17.3 | 12.7 |
| L1210 | 39.3** | −2.7 |
| P388 | 37.6** | 6.7 |
| MH-134 | 30.9 | 6.5 |
| C1498 | 54.2* | 8.8 |
| 3LL | 73.2*** | 54.8*** |
| B16 | 20.7 | 5.6 |

[a]Serum dilution ratio.
*P < 0.001, P < 0.01, *P < 0.05

(3) Cytocidal effect of Streptococcal LTA-induced TNF on L-cells

A suspension of L-929 cells (1×10$^5$ cells/ml) in RPMI-1640 medium supplemented with 10% FCS was distributed in a microplate having 24 wells (0.5 ml/well), and the cells were incubated for 3 hours at 37° C. under 5% CO$_2$-air. Then, to the cells in each well was added 0.5 ml of the TNF sample obtained in above (1) diluted 1:100 with RPMI-1640 containing 10% FCS. The culture was then continued for a further 48 hours.

At the end of the cultivation, the numbers of viable and dead cells in the medium and in the cell suspension released from the microplate by trypsin-EDTA method were counted under a phase contrast microscope.

TABLE 4

Cytocidal effect of streptococcal LTA-induced TNF on L-cells

| Serum specimen from mice treated with[a] | | Number of viable cells/ Number of dead cells[b] (× 10$^{-4}$/ml) | Cytotoxicity[c] (%) |
|---|---|---|---|
| P. acnes | LTA | | |
| − | − | 214/7 | 3.2 |
| + | − | 208/11 | 5.0 |
| − | + | 206/12 | 5.5 |
| + | + | 3/87 | 96.7 |
| RPMI-1640 | | 215/8 | 3.6 |
| with 10% FCS | | | |

[a]Samples were 100 fold diluted with RPMI-1640 containing 10% FCS, and submitted to the assay.
[b]Values are the average of duplicate counts.
[c]Cytotoxicity was calculated by the equation:

$$\frac{\text{Number of dead cells}}{\text{Number of viable cells}} \times 100\ (\%)$$

(4) Induction of tumor necrosis by Streptococcal LTA-induced TNF

Necrosis of tumor mass caused by LTA-induced TNF was studied according to the method of Carswell et al. (Proc. Nat. Acad. Sci. USA, 72 (9), 3666–3670, 1975). A group of 4 female, 5 week-old BALB/c mice (Charles River Japan Inc.) were given an intradermal implantation of 2×10$^5$ cells/mouse of Meth-A fibrosarcoma. Seven days after the transplantation, when the tumor mass reached 7–8 mm in diameter, 0.3 ml of the TNF sample obtained in above (1) was injected twice from the tail vein at a time interval for 3 hours.

Twenty-four hours after the second administration, necrosis of the tumor was evaluated by the grading system of Carswell et al. (ibid.). As shown in Table 5, the injection of serum of mice treated with P. acnes and LTA caused the necrosis of established-sarcoma in all mice.

TABLE 5

Necrosis of sarcoma Meth-A by streptococcal LTA-induced TNF

| Serum specimen from mice treated with | | Necrotic response[a] (number of mice) | | | |
|---|---|---|---|---|---|
| P. acnes | LTA | − | + | ++ | +++ |
| − | − | 4 | 0 | 0 | 0 |
| + | − | 4 | 0 | 0 | 0 |
| − | + | 4 | 0 | 0 | 0 |
| + | + | 0 | 2 | 2 | 0 |
| RPMI-1640 with 10% FCS | | 4 | 0 | 0 | 0 |

[a]The grading system of Carswell et al. was adopted as follows:
− ... no observable change
+ ... 25–50% portion of tumor mass underwent necrosis
++ ... 50–75% portion of tumor mass underwent necrosis
+++ ... more than 75% portion of tumor mass underwent necrosis

EXAMPLE 5

Lethal toxicity of streptococcal LTA in mice

LTA obtained in the Preparation Example was given by intraperitoneal injection at varying doses of 125–40,000 μg/mouse to groups of 4 female, 5 week-old BALB/c mice (Charles River Japan Inc.) with or without previous priming with P. acnes. The results are shown in Table 6. The data also include lethal toxicity of an endotoxic lipopolysaccharide (LPS, prepared from Salmonella enteritidis, Difco Lipopolysaccharide W, USA) as a reference.

TABLE 6

Lethal toxicity of streptococcal LTA by intraperitoneal injection

| Dose (μg/mouse) | Normal mice LTA (dead[b]/total) | Normal mice LPS (dead[b]/total) | P. acnes primed mice[a] LTA (dead[b]/total) | P. acnes primed mice[a] LPS (dead[b]/total) |
|---|---|---|---|---|
| 40000 | 0/4 | | | |
| 20000 | 0/4 | | | |
| 2000 | 0/4 | | | |
| 1000 | NT[c] | 4/4 | 0/4 | |
| 500 | NT[c] | 4/4 | 0/4 | |
| 250 | NT[c] | 2/4 | 0/4 | |
| 125 | 0/4 | 0/4 | | |
| 12.5 | | | | 4/4 |
| 6.25 | | | | 4/4 |
| 3.13 | | | | 4/4 |
| 1.56 | | | | 3/4 |
| 0.8 | | | | 2/4 |
| 0.4 | | | | 0/4 |

[a]Priming by intraperitoneal administration of formalin-killed *P. acnes* (1.5 mg/mouse) was conducted 12 days before LTA injection.
[b]The number of dead animals was scored 3 days after LTA injection
[c]NT: Not tested None of the normal mice died by the injection of 40,000 μg of LTA, while 500 μg and 250 μg of a reference LPS killed all and half of each group of 4 test mice, respectively.

With *P. acnes*-primed mice under the experimental condition adopted for TNF production, all of 4 test mice receiving 3.13 μg of LPS were killed. In sharp contrast with this, no death was scored with those injected with as high a dose as 1,000 μg of LTA. No signs of toxocities (diarrhea, ataxic gait) were observed in any of the mice administered with LTA.

Formulation Example

LTA injections

LTA (0.5 g) was dissolved in distilled water together with 10 g of mannitol and the volume was adjusted to 200 ml. After a filtration of the solution through a filter membrane (millipore filter ®, 0.22 μm), 2 ml aliquots of the filtrate were placed in vials under sterilized conditions, followed by lyophilization by a conventional method. The resulting vials, each containing 5 mg of LTA, can be used for injection after dissolving in 2 ml of distilled water or physiological saline for injection.

LTA capsules

LTA (15 g) and mannitol (55 g) were mixed homogeneously. 70 mg portions of the mixed powder were filled in No. 4 gelatin capsules of the Japanese Pharmacopoeia. The resulting capsules, containing 15 mg of LTA in each capsule, passed Disintegration Test for Capsules in accordance with the Japanese Pharmacopoeia.

We claim:

1. A method for inducing the production of TNF in a mammal comprising administering to the mammal a sufficient amount of lipoteichoic acid (LTA) to induce TNF in the mammal.

2. The method of claim 1 wherein the LTA is administered in dosage units containing from about 0.1 to about 100 mg LTA per dosage unit.

3. The method of claim 2 wherein the LTA is administered in dosage units containing from about 1 to about 20 mg of LTA per dosage unit.

4. The method of claim 1 wherein the LTA is obtained from *Streptococcus pyogenes*.

5. The method of claim 1 wherein the LTA is obtained from *Lactobacillus plantarum*.

6. The method of claim 1 wherein the LTA is administered orally.

7. The method of claims 1 wherein the LTA is administered intraperitoneally.

8. The method of claim 1 wherein the LTA is administered in combination with a pharmaceutically acceptable diluent or carrier selected from the group consisting of lactose, crystalline cellulose, corn starch, glucose, magnesium stearate, and calcium stearate.

9. The method of claim 1 wherein the LTA is obtained from bacteria selected from the group consisting of *Streptococcus faecalis, Streptococcus mutans, Streptococcus lactis, Streptococcus equisimilis, Streptococcus sanguis, Staphylococcus aureus, Staphylococcus epidermidis, Lactobacillus fermentum, Lactobacillus casei*, and *Listera monocytogenes*.

10. A method of treating solid or ascites Meth-A-fibrosarcoma in a mammal comprising administering to the mammal an effective amount of LTA.

11. A method of treating solid or ascites tumors in a mammal comprising administering to the mammal an effective amount of LTA.

* * * * *

UNITED STATES PATENT AND TRADEMARK OFFICE
CERTIFICATE OF CORRECTION

PATENT NO. : 4,678,773

DATED : July 7, 1987

INVENTOR(S) : USAMI et al.

It is certified that error appears in the above-identified patent and that said Letters Patent is hereby corrected as shown below:

On the title page, "11 Claims, 2 Drawing Figures" should read
-- 11 Claims 3 Drawing Figures --.

In the drawing , Figs. 1, 2 and 3, should appear as shown on the attached sheets.

Signed and Sealed this

Fourteenth Day of February, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,678,773
DATED : July 7, 1987
INVENTOR(S) : USAMI et al

It is certified that error appears in the above—identified patent and that said Letters Patent is hereby corrected as shown below:

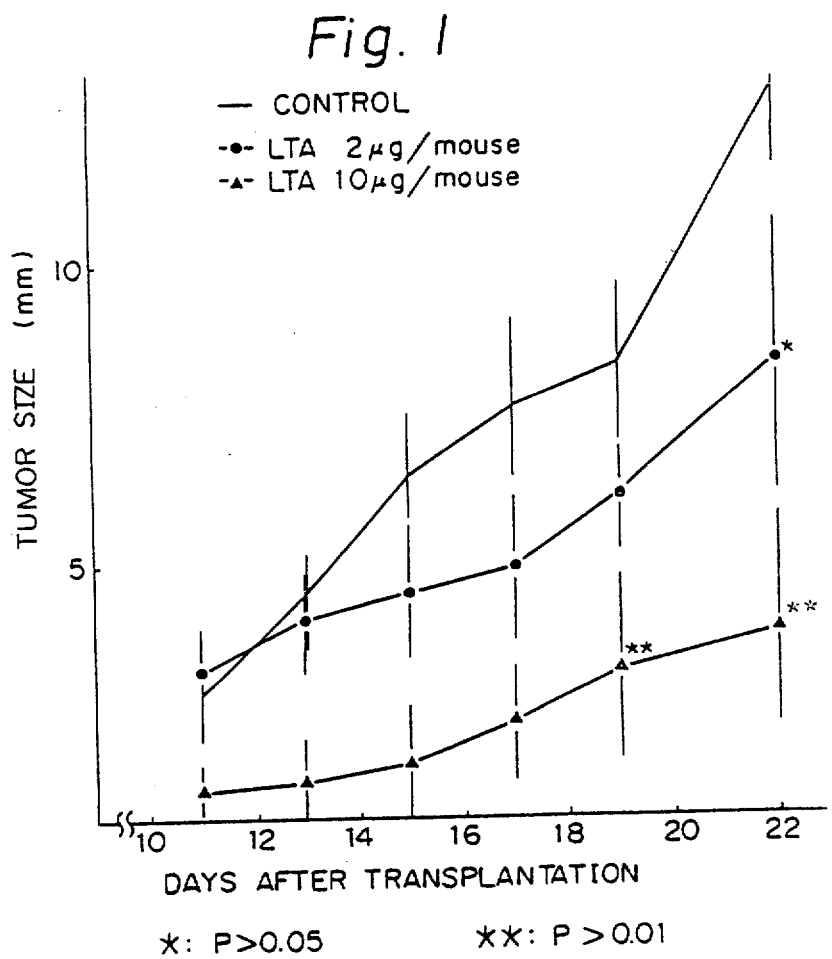

Fig. 1

\*: $P > 0.05$ \quad \*\*: $P > 0.01$

UNITED STATES PATENT AND TRADEMARK OFFICE
CERTIFICATE OF CORRECTION

PATENT NO. : 4,678,773

DATED : July 7, 1987

INVENTOR(S) : USAMI et al

It is certified that error appears in the above-identified patent and that said Letters Patent is hereby corrected as shown below:

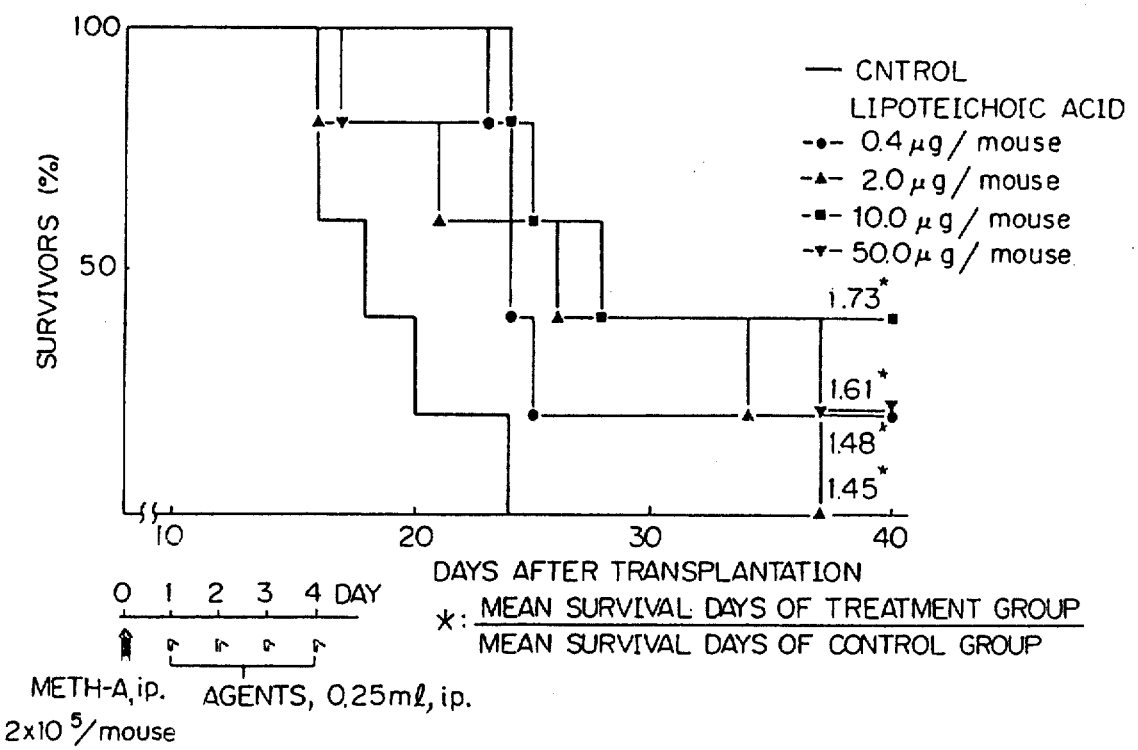

Fig. 2 ANTITUMOR ACTIVITY OF LIPOTEICHOIC ACID FROM STREPTOCOCCUS PYOGENES Sv

UNITED STATES PATENT AND TRADEMARK OFFICE
CERTIFICATE OF CORRECTION

PATENT NO. : 4,678,773

DATED : July 7, 1987

INVENTOR(S) : USAMI et al

It is certified that error appears in the above—identified patent and that said Letters Patent is hereby corrected as shown below:

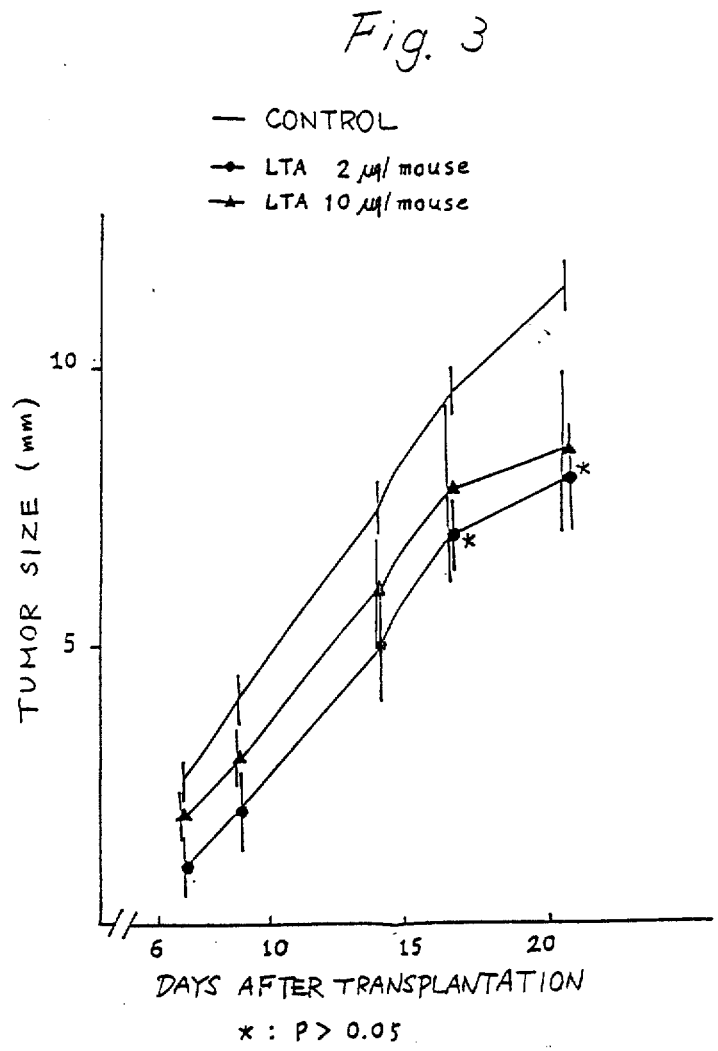

Fig. 3